(12) United States Patent
Cruise et al.

(10) Patent No.: US 9,655,989 B2
(45) Date of Patent: May 23, 2017

(54) POLYMERIC TREATMENT COMPOSITIONS

(71) Applicant: MicroVention, Inc., Tustin, CA (US)

(72) Inventors: Gregory M. Cruise, Rancho Santa Margarita, CA (US); Michael J. Constant, Mission Viejo, CA (US); Edward Michael Keeley, Huntington Beach, CA (US); Rob Greene, Tustin, CA (US); Clayton Harris, Tustin, CA (US)

(73) Assignee: MicroVention, Inc., Tustin, CA (US)

( * ) Notice: Subject to any disclaimer, the term of this patent is extended or adjusted under 35 U.S.C. 154(b) by 0 days.

(21) Appl. No.: 14/736,145

(22) Filed: Jun. 10, 2015

(65) Prior Publication Data

US 2016/0243273 A1    Aug. 25, 2016

Related U.S. Application Data

(63) Continuation of application No. 14/054,515, filed on Oct. 15, 2013, now Pat. No. 9,078,950.

(60) Provisional application No. 61/714,102, filed on Oct. 15, 2012.

(51) Int. Cl.
| | |
|---|---|
| *A61L 24/06* | (2006.01) |
| *A61K 9/12* | (2006.01) |
| *A61L 24/00* | (2006.01) |
| *A61K 49/04* | (2006.01) |
| *A61K 49/12* | (2006.01) |

(52) U.S. Cl.
CPC .......... *A61L 24/06* (2013.01); *A61K 49/0442* (2013.01); *A61K 49/12* (2013.01); *A61L 24/001* (2013.01); *A61L 24/0015* (2013.01); *A61L 2300/44* (2013.01); *A61L 2400/06* (2013.01); *A61L 2430/36* (2013.01)

(58) Field of Classification Search
USPC .................................. 523/117, 105; 528/182
See application file for complete search history.

(56) References Cited

U.S. PATENT DOCUMENTS

| | | | |
|---|---|---|---|
| 4,406,878 A | 9/1983 | Boer et al. | |
| 5,580,568 A | 12/1996 | Greff et al. | |
| 5,667,767 A | 9/1997 | Greff et al. | |
| 5,695,480 A | 12/1997 | Evans et al. | |
| 5,702,361 A | 12/1997 | Evans et al. | |
| 5,755,658 A | 5/1998 | Wallace et al. | |
| 5,823,198 A | 10/1998 | Jones et al. | |
| 5,830,178 A | 11/1998 | Jones et al. | |
| 5,851,508 A | 12/1998 | Greff et al. | |
| 5,894,022 A | 4/1999 | Ji et al. | |
| 6,004,573 A | 12/1999 | Rathi et al. | |
| 6,017,977 A | 1/2000 | Evans et al. | |
| 6,037,366 A | 3/2000 | Krall et al. | |
| 6,040,408 A | 3/2000 | Koole | |
| 6,051,607 A | 4/2000 | Greff | |
| 6,146,373 A | 11/2000 | Cragg et al. | |
| 6,281,263 B1 | 8/2001 | Evans et al. | |
| 6,303,100 B1 | 10/2001 | Ricci et al. | |
| 6,333,020 B1 | 12/2001 | Wallace et al. | |
| 6,335,384 B1 | 1/2002 | Evans et al. | |
| 6,342,202 B1 | 1/2002 | Evans et al. | |
| 6,454,738 B1 | 9/2002 | Tran et al. | |
| 6,475,477 B1 | 11/2002 | Kohn et al. | |
| 6,503,244 B2 | 1/2003 | Hayman | |
| 6,511,468 B1 | 1/2003 | Cragg et al. | |
| 6,511,472 B1 | 1/2003 | Hayman et al. | |
| 6,531,111 B1 | 3/2003 | Whalen et al. | |
| 6,558,367 B1 | 5/2003 | Cragg et al. | |
| 6,562,362 B1 | 5/2003 | Bae et al. | |
| 6,565,551 B1 | 5/2003 | Jones et al. | |
| 6,569,190 B2 | 5/2003 | Whalen et al. | |
| 6,599,448 B1 | 7/2003 | Ehrhard et al. | |
| 6,602,269 B2 | 8/2003 | Wallace et al. | |
| 6,623,450 B1 | 9/2003 | Dutta et al. | |
| 6,645,167 B1 | 11/2003 | Whalen et al. | |
| 6,699,222 B1 | 3/2004 | Jones et al. | |
| 6,756,031 B2 | 6/2004 | Evans et al. | |
| 6,759,028 B2 | 7/2004 | Wallace et al. | |
| 6,962,689 B2 | 11/2005 | Whalen et al. | |
| 6,964,657 B2 | 11/2005 | Cragg et al. | |
| 6,979,464 B2 | 12/2005 | Gutowska | |
| 7,018,365 B2 | 3/2006 | Strauss et al. | |
| 7,070,607 B2 | 7/2006 | Murayama et al. | |
| 7,083,643 B2 | 8/2006 | Whalen et al. | |
| 7,138,106 B2 | 11/2006 | Evans et al. | |
| 7,374,568 B2 | 5/2008 | Whalen et al. | |
| 7,459,142 B2 | 12/2008 | Greff | |

(Continued)

FOREIGN PATENT DOCUMENTS

| | | |
|---|---|---|
| CA | 2551373 C | 6/2014 |
| CN | 101513542 B | 8/2012 |

(Continued)

OTHER PUBLICATIONS

Dudeck O, Jordan O, Hoffmann KT, et al. Embolization of experimental wide-necked aneurysms with iodine-containing polyvinyl alcohol solubilized in a low-angiotoxicity solvent. AJNR Am J Neuroradiol. 2006;27(9):1849-1855.

Dudeck O, Jordan O, Hoffmann KT, et al. Organic solvents as vehicles for precipitating liquid embolics: a comparative angiotoxicity study with superselective injections of swine rete mirabile. AJNR Am J Neuroradiol. 2006;27(9):1900-1906.

Onyx Liquid Embolic System Onyx HD-500, Instructions for Use, ev3 Endovascular, Inc., Nov. 2007.

(Continued)

*Primary Examiner* — Tae H Yoon
(74) *Attorney, Agent, or Firm* — K&L Gates LLP; Louis C. Cullman; Brian J. Novak

(57) ABSTRACT

Polymeric compositions are described comprising a biocompatible polymer including a biodegradable linkage to a visualization agent and a non-physiological pH solution; wherein the biocompatible polymer is soluble in the non-physiological pH solution and insoluble at a physiological pH. Methods of forming the solutions and polymers are disclosed as well as methods of therapeutic use.

15 Claims, 3 Drawing Sheets

(56) References Cited

U.S. PATENT DOCUMENTS

| | | |
|---|---|---|
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,776,063 B2 | 8/2010 | Sawhney et al. |
| 7,790,141 B2 | 9/2010 | Pathak et al. |
| 7,838,699 B2 | 11/2010 | Schwarz et al. |
| 7,976,527 B2 | 7/2011 | Cragg et al. |
| 8,066,667 B2 | 11/2011 | Hayman et al. |
| 8,235,941 B2 | 8/2012 | Hayman et al. |
| 8,454,649 B2 | 6/2013 | Cragg et al. |
| 8,486,046 B2 | 7/2013 | Hayman et al. |
| 8,492,329 B2 * | 7/2013 | Shemesh .............. C07K 14/47 514/1.1 |
| 8,685,367 B2 | 4/2014 | Brandom et al. |
| 9,078,950 B2 * | 7/2015 | Cruise .................. A61L 24/06 |
| 2001/0022962 A1 | 9/2001 | Greff et al. |
| 2001/0024637 A1 | 9/2001 | Evans et al. |
| 2001/0033832 A1 | 10/2001 | Wallace et al. |
| 2001/0036451 A1 | 11/2001 | Goupil et al. |
| 2001/0046518 A1 | 11/2001 | Sawhney |
| 2002/0026234 A1 | 2/2002 | Li et al. |
| 2002/0042378 A1 | 4/2002 | Reich et al. |
| 2003/0021762 A1 | 1/2003 | Luthra et al. |
| 2003/0040733 A1 | 2/2003 | Cragg et al. |
| 2003/0100942 A1 | 5/2003 | Ken et al. |
| 2003/0211083 A1 | 11/2003 | Vogel et al. |
| 2003/0232198 A1 | 12/2003 | Lamberti et al. |
| 2004/0024098 A1 | 2/2004 | Mather et al. |
| 2004/0091425 A1 | 5/2004 | Boschetti |
| 2004/0091543 A1 | 5/2004 | Bell et al. |
| 2004/0157082 A1 * | 8/2004 | Ritter .................. B82Y 25/00 428/611 |
| 2004/0158282 A1 | 8/2004 | Jones et al. |
| 2004/0209998 A1 | 10/2004 | De Vries |
| 2004/0224864 A1 | 11/2004 | Patterson et al. |
| 2004/0228797 A1 | 11/2004 | Bein et al. |
| 2005/0003010 A1 | 1/2005 | Cohen et al. |
| 2005/0008610 A1 | 1/2005 | Schwarz et al. |
| 2005/0106119 A1 | 5/2005 | Brandom et al. |
| 2005/0123596 A1 | 6/2005 | Kohane et al. |
| 2005/0143484 A1 | 6/2005 | Fang et al. |
| 2005/0175709 A1 | 8/2005 | Baty et al. |
| 2005/0196449 A1 | 9/2005 | DiCarlo et al. |
| 2005/0226935 A1 | 10/2005 | Kamath et al. |
| 2005/0244504 A1 | 11/2005 | Little et al. |
| 2005/0265923 A1 | 12/2005 | Toner et al. |
| 2006/0008499 A1 | 1/2006 | Hudak |
| 2006/0067883 A1 | 3/2006 | Krom et al. |
| 2006/0088476 A1 | 4/2006 | Harder et al. |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237741 A1 | 10/2007 | Figuly et al. |
| 2007/0248567 A1 | 10/2007 | Pathak et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0214695 A1 | 9/2008 | Pathak et al. |
| 2008/0226741 A1 | 9/2008 | Richard |
| 2008/0243129 A1 | 10/2008 | Steffen et al. |
| 2008/0269874 A1 | 10/2008 | Wang et al. |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0093550 A1 | 4/2009 | Rolfes et al. |
| 2009/0117033 A1 | 5/2009 | O'Gara |
| 2009/0117070 A1 | 5/2009 | Daniloff et al. |
| 2009/0181068 A1 | 7/2009 | Dunn |
| 2009/0186061 A1 | 7/2009 | Griguol et al. |
| 2009/0215923 A1 | 8/2009 | Carnahan et al. |
| 2009/0221731 A1 | 9/2009 | Vetrecin et al. |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0049165 A1 | 2/2010 | Sutherland et al. |
| 2010/0080788 A1 | 4/2010 | Barnett et al. |
| 2010/0086678 A1 | 4/2010 | Arthur et al. |
| 2010/0247663 A1 | 9/2010 | Day et al. |
| 2010/0256777 A1 | 10/2010 | Datta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0071495 A1 | 3/2011 | Tekulve |
| 2011/0091549 A1 | 4/2011 | Blaskovich et al. |
| 2011/0182998 A1 | 7/2011 | Reb et al. |
| 2011/0190813 A1 | 8/2011 | Brownlee et al. |
| 2011/0202016 A1 | 8/2011 | Zugates et al. |
| 2012/0041481 A1 | 2/2012 | Daniloff et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Bartling et al. |
| 2012/0238644 A1 | 9/2012 | Gong et al. |
| 2012/0244198 A1 | 9/2012 | Malmsjo et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0184660 A1 | 7/2013 | Swiss et al. |
| 2013/0225778 A1 * | 8/2013 | Goodrich .............. A61K 49/0442 526/270 |
| 2013/0336917 A1 | 12/2013 | Cruise et al. |
| 2014/0039459 A1 | 2/2014 | Folk et al. |
| 2014/0056806 A1 | 2/2014 | Vernengo et al. |
| 2014/0107251 A1 | 4/2014 | Cruise et al. |
| 2014/0171907 A1 | 6/2014 | Golzarian et al. |
| 2014/0274945 A1 | 9/2014 | Blaskovich et al. |
| 2014/0277057 A1 | 9/2014 | Ortega et al. |
| 2016/0243157 A1 | 8/2016 | Cruise et al. |

FOREIGN PATENT DOCUMENTS

| | | |
|---|---|---|
| CN | 102107025 B | 5/2014 |
| EP | 1599258 B1 | 8/2008 |
| EP | 1601392 B1 | 4/2009 |
| EP | 1558299 B1 | 12/2012 |
| WO | 2005/013810 A2 | 2/2005 |
| WO | 2011/110589 A1 | 9/2011 |
| WO | 2012/025023 A1 | 3/2012 |
| WO | 2012/088896 A1 | 7/2012 |
| WO | 2012/171478 A1 | 12/2012 |
| WO | 2014/152488 A2 | 9/2014 |

OTHER PUBLICATIONS

Takao H, Murayama Y, Yuki I, et al. Endovascular treatment of experimental aneurysms using a combination of thermoreversible gelation polymer and protection devices: feasibility study. Neurosurgery. 2009;65(3):601-609.

Argawal et al., Chitosan-based systems for molecular imaging. Advanced Drug Delivery Reviews, 62:42-48 (2010).

Supplementary European Search Report mailed on Sep. 26, 2016 for European Patent Application No. 13846860.8 filed on Oct. 15, 2013.

* cited by examiner

POLYMERIC TREATMENT COMPOSITIONS

CROSS REFERENCE TO RELATED APPLICATIONS

This application is a continuation of U.S. patent application Ser. No. 14/054,515, filed Oct. 15, 2013, now U.S. Pat. No. 9,078,950, which claims the benefit of U.S. provisional patent application No. 61/714,102, filed Oct. 15, 2012, the entire disclosures each of which are incorporated herein by reference.

FIELD

The present invention relates generally to vascular treatment compositions and methods of using these compositions to treat vascular conditions. The compositions can comprise a polymer(s) that transitions from a liquid to a solid upon being subject to physiological conditions.

BACKGROUND

Embolization is widely used to treat vascular malformations, such as aneurysms, arteriovenous malformations, fistulas, and tumors. These malformations can be treated with a variety of different products, including metallic coils, polymer-metal hybrid coils, microparticles, and foams. However, there remains a need for products that can minimize risks associated with embolization.

SUMMARY

Polymeric compositions are described which comprise: a biocompatible polymer including a biodegradable linkage to a visualization agent, and a non-physiological solution; wherein the biocompatible polymer is soluble in the non-physiological solution and insoluble at physiological conditions.

Polymeric compositions are described which comprise: a biocompatible polymer including a biodegradable linkage to a visualization agent, and a water-miscible organic solvent; wherein the biocompatible polymer is soluble in the organic solvent and insoluble at physiological conditions.

Methods are also described for use of the polymeric compositions. In one embodiment, methods are described comprising injecting through a delivery device into a physiological environment a liquid embolic composition comprising: a biocompatible polymer including a biodegradable linkage to a visualization agent, and a non-physiological solution, wherein the biocompatible polymer precipitates when it reaches the physiological conditions.

In one embodiment, methods are described comprising injecting through a delivery device into a vessel with physiological environment a liquid embolic composition comprising: a biocompatible polymer including a biodegradable linkage to a visualization agent, and a water-miscible organic solvent, wherein the biocompatible polymer precipitates when it reaches the physiological conditions and treats the vascular disorder.

The biodegradable linkage can be cleaved by hydrolysis and/or enzymatic cleavage. Biodegradable linkages susceptible to enzymatic cleavage can be esters or amino acids such as Seq. ID 1, Seq. ID 2, Seq. ID 3, Seq. ID 4, Seq. ID 5, Seq. ID 6, Seq. ID 7, Seq. ID 8, Seq. ID 9, Seq. ID 10, Seq. ID 11, Seq. ID 12, or Seq. ID 13. Biodegradable linkages susceptible to hydrolysis can be an ester, a carbonate, or a polyester.

The biodegradable linked contrast/visualization agent can be an iodinated compound.

The biocompatible polymer can be a reaction product of two or more different monomers and can have a concentration of about 1% w/w to about 50% w/w.

The non-physiological solution can be aqueous and can have a pH of less than about 5 or a pH of greater than about 8.

In one embodiment, a composition for filling a vascular defect is described comprising: an aqueous solution at non-physiological pH; a biocompatible polymer including a pH sensitive component and a biodegradable linkage to a visualization agent at a concentration of from about 1% to 50% w/w, that is soluble in the aqueous solution at non-physiological pH and insoluble at physiological conditions.

In another embodiment, methods are described comprising: providing a liquid embolic composition comprising a biocompatible polymer including a biodegradable linkage to a visualization agent, and a non-physiological pH aqueous solution, wherein the biocompatible polymer is soluble in the non-physiological pH aqueous solution and insoluble in at physiological conditions; inserting a delivery device into a vessel; guiding the delivery device to an area in need of treatment wherein the area has physiological conditions; injecting the liquid embolic polymer composition through the delivery device into the vessel at the area in need of treatment thereby immediately precipitating the polymer and forming a solid polymeric mass; and treating the vascular condition.

In one embodiment, a composition for filling a vascular defect is described comprising: a water-miscible organic solvent; a biocompatible polymer at a concentration of from about 1% to 50% w/w including a biodegradable linkage to a visualization agent, which is soluble in the organic solvent and insoluble at physiological conditions.

In another embodiment, methods are described comprising: providing a liquid embolic composition comprising a biocompatible polymer including a biodegradable linkage to a visualization agent, and a water-miscible organic solvent, wherein the biocompatible polymer is soluble in the organic solvent and insoluble in at physiological conditions; inserting a delivery device into a vessel; guiding the delivery device to an area in need of treatment; injecting the liquid embolic polymer composition through the delivery device into the vessel at the area in need of treatment thereby immediately precipitating the polymer and forming a solid polymeric mass; and treating the vascular condition.

DETAILED DESCRIPTION

Figure 1:
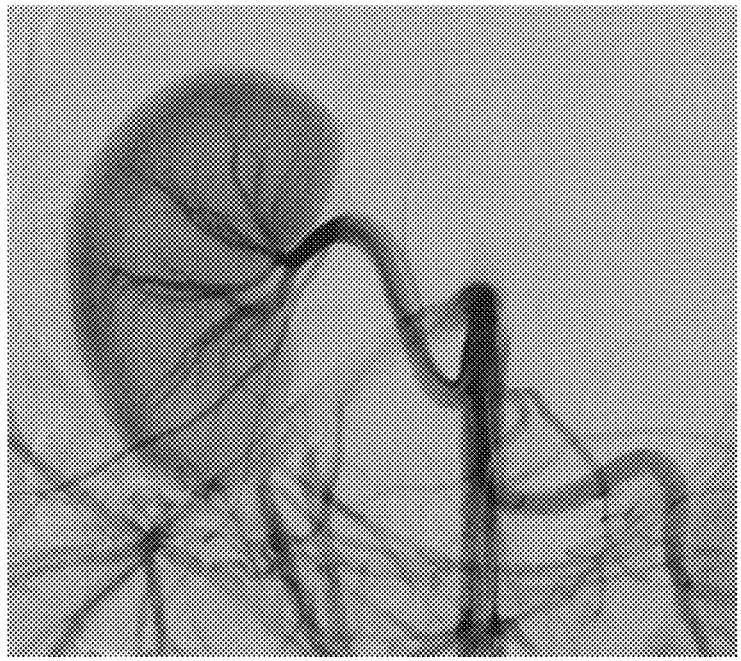
FIG. 1 illustrates a pre-treatment angiogram of a rabbit kidney before use of an embodiment of an embolic polymer.

Described herein generally are polymeric treatment compositions comprising a biocompatible polymer including a visualization species coupled to the polymer by a biodegradable linkage, wherein the biocompatible polymer can be soluble in selected solvent systems and insoluble at physiological conditions or in a physiological solution/fluid in a selected solvent. In some embodiments, the visualization species can be an opacification agent(s) that can permit visualization in vivo. In other embodiments, the solution can include a miscible solvent that can dissolve the polymer. In other embodiments, the solution can include a non-physiological pH solvent. These compositions can be introduced through a delivery device in the liquid state and transition to the solid state once in contact with a physiological fluid.

When a polymer is soluble in solution, it can be easy to deploy through a delivery device, e.g. microcatheter, to a delivery site and/or treatment site. However, once precipitated out of solution, a polymer can be much more difficult to deploy. For example, once precipitated, a polymer can in some instances be more difficult to deploy through a delivery device. As such, the compositions and methods described herein can provide polymer treatment solutions to sites that would otherwise not be easily administered to without being soluble prior to exiting a delivery device.

The compositions can comprise a solution at a non-physiological condition (e.g. non-physiological pH). The solution can include a polymer soluble in the solution but insoluble at physiological conditions; the polymer can include a visualization agent biodegradably attached to it. In some embodiments, the solution can include a polymer soluble in a non-physiological pH aqueous solution but insoluble at physiological conditions. In another embodiment, the polymer can be soluble in a water-miscible organic solvent but insoluble at physiological conditions (e.g. water).

A function of the biocompatible polymer, e.g. liquid embolic polymer, can be to precipitate when coming in contact with blood or other physiological fluid. If the pH of the physiological fluid is the solubility trigger, the physiological pH can be a pH of about 7.0, about 7.1, about 7.2, about 7.3, about 7.4, about 7.5, about 7.6, about 7.7 or about 7.8, between about 7.0 and about 7.8, between about 7.1 and about 7.7, between about 7.2 and about 7.6, or any value in a range bound by or between any of these values. The non-physiological pH can be a pH between about 1.0 and about 6.9, or about 2.0 and about 6.0, about 7.9 and about 12.0, about 8.5 and about 10.0. Alternatively, if the solubility trigger is solubility in a water miscible organic solvent and insolubility at physiological conditions, any physiological environment can initiate the precipitation.

Precipitation of the polymer at physiological conditions can be used to occlude a biological structure. Control of the liquid embolic polymer's solubility can be achieved by selection of the composition of the polymer. The polymer can be prepared with monomers having ionizable moieties. In some embodiments, the polymers can be a reaction product of two different monomers, three different monomers, four different monomers, five different monomers, or more. In the case of a pH sensitive solubility trigger, a hydrophobic polymer can be constructed with a minimum amount of ionizable moieties to render the polymer soluble in non-physiological pH solutions. The ratio of monomers with ionizable moieties and other monomers can be dependent on the structure of the monomers and can be determined experimentally.

Polymers sensitive to pH such as amino-containing liquid embolic polymers can be dissolved in a low pH solution, the amines may be substantially protonated and can enhance the solubility of the polymer. The resulting solution can be placed in conditions with physiological pH and the amines can deprotonate and render the polymer insoluble. Conversely, carboxylic acid-containing polymers can be dissolved in a high pH solution, the carboxylic acids can be substantially deprotonated and enhance the solubility of the polymer. The resulting solution can be placed in conditions with physiological pH and the carboxylic acids can protonate and render the polymer insoluble.

A monomer or monomers can include at least one visualization species linked to the monomer to impart visibility of the liquid embolic polymer when imaged using a medically relevant imaging technique such as fluoroscopy, computed tomography, or magnetic resonance techniques. Characteristic features of the monomers with visualization species can be cores that are visible under medically relevant imaging techniques and a polymerizable moiety attached to the core with a biodegradable linkage.

A visualization agent can also be linked after polymerization if a reactive pendent group is added to the polymerization mixture before polymerization. An exemplary reactive pendent group can be an acrylate monomer having an epoxide pendent group (e.g., glycidyl acetate) or a hydroxyl ethyl pendent group. A skilled artisan can envision other pendent groups that can be added to a formed polymer.

Visualization of the polymer under fluoroscopy and CT imaging can be imparted by the use of monomers with cores containing iodine, particularly aromatic rings with a plurality of iodine atoms. A core containing iodine can be triiodophenol. Concentrations of iodine to render the liquid embolic visible using fluoroscopy or CT imaging can range from about 10% to about 60% w/w, about 20% to about 50% w/w, or about 30% to about 40% w/w of the liquid embolic solution. Visualization of the polymer under magnetic resonance imaging can be imparted by the incorporation of monomers containing gadolinium. A visualization agent for magnetic resonance imaging can be gadolinium diethylenetriaminepentaacetic acid aminoethylmethacrylate. Concentrations of gadolinium to render the liquid embolic visible using magnetic resonance imaging can range from about 0.1% to about 1% w/w, about 0.5% to about 1% w/w, or about 0.1% to about 0.5% w/w of the liquid embolic solution.

Some monomers can contain a polymerizable moiety and optionally an ionizable moiety. Polymerizable moieties can be those that permit free radical or anionic polymerization, including but not limited to acrylates, methacrylates, acrylamides, methacrylamides, vinyl groups, and derivatives thereof. Alternatively, other reactive chemistries can be employed to polymerize the liquid embolic polymer, such as, but not limited to nucleophile/N-hydroxysuccinimde esters, nucleophile/halide, vinyl sulfone/acrylate or maleimide/acrylate. Preferred polymerizable moieties can be acrylates and acrylamides.

Other monomers can contain a polymerizable moiety and can have a structure that is conducive to desired solubility characteristics. Polymerizable moities can be those that permit free radical polymerization, including but not limited to acrylates, methacrylates, acrylamides, methacrylamides, vinyl groups, and derivatives thereof. Alternatively, other reactive chemistries can be employed to polymerize the liquid embolic polymer, i.e. nucleophile/N-hydroxysuccinimde esters, nucleophile/halide, vinyl sulfone/acrylate or maleimide/acrylate. Preferred polymerizable moieties can be acrylates and acrylamides. In general, other monomers can compensate for monomers including visualization species.

If a polymer is too hydrophobic for dissolution in a water miscible solvent, more hydrophilic monomers can be introduced to alter the solubility. If a polymer is too hydrophilic and is soluble in water, more hydrophobic monomers can be introduced to alter the solubility. Other monomers can include hydroxyethyl methacrylate, t-butyl acrylate, t-butyl acrylamide, n-octyl methacrylate, and methyl methacrylate. Such monomers can be present at a concentration of about 1% w/w to about 50% w/w, about 1% w/w to about 40% w/w, about 1% w/w to about 30% w/w, about 1% w/w to about 20% w/w, about 1% w/w to about 15% w/w, about 1% w/w to about 10% w/w, about 2% w/w to about 15% w/w, about 2% w/w to about 20% w/w, about 2% w/w to about 10% w/w, about 1% w/w, about 2% w/w, about 3% w/w, about 4% w/w, about 5% w/w, about 6%, about 7% w/w, about 8%, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, or about 25% w/w.

Some monomers can include biodegradable linkages to visualization species. Biodegradable linkages can permit separation of the visualization core from the polymer. After separating from the polymer, the core can be removed by diffusion and/or by cells comprising the foreign body response to the polymer. Biodegradable linkages can be separated into two types. The two types can include those susceptible to hydrolysis and those susceptible to enzymatic action. Linkages susceptible to hydroylsis can generally include esters, polyesters, or carbonates.

The biodegradable linkages can be introduced into monomers or the polymers after formation. One skilled in the art can envision benefits to both methods of introducing biodegradable linkages into the polymers.

Ester linkages can be introduced by reacting hydroxyl groups with cyclic anhydrides, such as succinic or glutaric anhydride, or cylic esters, such as lactide, glycolide, ϵ-caprolactone, and trimethylene carbonate. The rate of degradation can be controlled by ester selection and the number of esters inserted into biodegradable linkages.

Linkages susceptible to enzymatic action can include peptides that can be degraded by enzymes, such as but not limited to matrix metalloproteinases, collagenases, elastases, cathepsin, or a combination thereof. Peptide sequences degraded by matrix metalloproteinases can include Gly-Pro-Gln-Gly-Ile-Ala-Ser-Gln (Seq. ID 1), Gly-Pro-Gln-Pro-Ala-Gly-Gln (Seq. ID 2), Gly-Pro-Gln-Gly-Ala-Gly-Gln (Seq. ID 3), Lys-Pro-Leu-Gly-Leu-Lys-Ala-Arg-Lys (Seq. ID 4), Gly-Pro-Gln-Ile-Trp-Gly-Gln (Seq. ID 5), and Gln-Pro-Gln-Gly-Leu-Ala-Lys (Seq. ID 6). Peptide sequences degraded by cathepsin can include Gly-Phe-Gln-Gly-Val-Gln-Phe-Ala-Gly-Phe (Seq. ID 7), Gly-Phe-Gly-Ser-Val-Gln-Phe-Ala-Gly-Phe (Seq. ID 8), and Gly-Phe-Gly-Ser-Thr-Phe-Phe-Ala-Gly-Phe (Seq. ID 9). Peptide sequences degraded by collagenase can include Gly-Gly-Leu-Gly-Pro-Ala-Gly-Gly-Lys (Seq. ID 10) and Ala-Pro-Gly-Leu (Seq. ID 11). Peptide sequences degraded by papain can include Gly-Phe-Leu-Gly (Seq. ID 12). Peptide sequences degraded by caspase-3 can include Asp-Glu-Val-Asp-Thr (Seq. ID 13)The rate of degradation can be controlled by the peptide sequence selection.

In one embodiment, liquid embolic polymers can be polymerized from solutions of monomers linked to visualization species and optionally other monomers, or from solutions of monomers whose later polymers are linked to visualization species. The solvent used to dissolve the monomers can be any solvent that dissolves the desired monomers. Solvents can include methanol, acetonitrile, dimethyl formamide, and dimethyl sulfoxide.

Polymerization initiators can be used to start the polymerization of the monomers. The polymerization can be initiated by reduction-oxidation, radiation, heat, or any other method known in the art. Radiation cross-linking of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

In one embodiment, the polymerization initiator can be azobisisobutyronitrile (AIBN) or a water soluble AIBN derivative (2,2'-azobis(2-methylpropionamidine) dihydrochloride). Other initiators can include N,N,N',N'-tetramethylethylenediamine, ammonium persulfate, benzoyl peroxides, azobisisobutyronitriles and combinations thereof. Initiator concentrations can be from about 0.1% w/w to about 5% w/w, about 0.5% w/w to about 3% w/w, about 0.25% w/w, about 0.5% w/w, about 0.75% w/w, about 1% w/w, about 1.25% w/w, about 1.50% w/w, about 1.75% w/w, or about 2% w/w, about 3%, about 4%, or about 5% of the mass of the monomers in solution, or any range or value within the listed percentages. The polymerization reaction can be performed at elevated temperatures, of about 30° C. to about 200° C., about 50° C. to about 100° C., about 50° C., about 60° C., about 70° C., about 80° C., about 90° C. or about 100° C. or can proceed at room temperature without heating. After the polymerization is completed, the polymer can be recovered by precipitation in a non-solvent and dried under vacuum.

A water-miscible organic solvent can dissolve the final liquid embolic polymer. Concentrations of the polymer in an organic solvent can be from about 1% to about 50%, about 2.5% to about 25%, about 5% to about 15%, about 2.5%, about 5%, about 7.5%, about 10%, about 12.5%, about 15%, about 17.5%, about 20%, about 22.5%, about 25%, about 30%, about 35%, about 40%, about 45%, or about 50%, or any percentage or range of percentages bound by the above percentages. Solvents can include methanol, acetonitrile, dimethyl formamide, dimethyl isosorbide, and dimethyl sulfoxide.

Also, if a pH sensitive monomer is used within the polymer, a non-physiological pH aqueous solution can dissolve the liquid embolic polymer. Polymer concentrations in an aqueous solution can be from about 1% to about 50%, about 2.5% to about 25%, about 5% to about 15%, about 2.5%, about 5%, about 7.5%, about 10%, about 12.5%, about 15%, about 17.5%, about 20%, about 22.5%, about 25%, about 30%, about 35%, about 40%, about 45%, or about 50%, or any percentage or range of percentages bound by the above percentages. The aqueous solution can contain a minimum amount of buffer to maintain a non-physiologic pH after dissolution of the liquid embolic polymer, but not adversely affect the pH of the patient after administration. Alternatively, a buffer may not be needed. Buffer concentrations can range from about 1 mM to about 100 mM, about 20 mM to about 80 mM, about 30 mM to about 70 mM, about 40 mM to about 60 mM, about 45 mM to about 55 mM, about 10 mM, about 20 mM, about 30 mM, about 40 mM, about 50 mM, about 60 mM, about 70 mM, about 80 mM, about 90 mM, about 100 mM or any concentration or range of concentrations within the values listed.

For liquid embolic polymers containing amines, buffers can include citrate and acetate and solution pHs can be from about 3 to about 6, from about 3 to about 5, about 3, about 4, about 5 or about 6. For liquid embolic polymers containing carboxylic acids, buffers can include carbonate, N-cyclohexyl-2-aminoethanesulfonic acid (CHES), N-cyclohexyl-2-hydroxyl-3-aminopropanesulfonic acid (CAMPSO), N-cyclohexyl-3-aminopropanesulfonic acid (CAPS), 3-[4-(2-Hydroxyethyl)-1-piperazinyl]propanesulfonic acid (HEPPS or EPPS), 3-(N-morpholino)propanesulfonic acid (MOPS), 4-(2-hydroxyethyl)-1-piperazineethanesulfonic acid (HEPES), 2-(N-morpholino)ethanesulfonic acid (MES) and 2-amino-2-methyl-1-propanol (AMP) and solution pH's can be from about 8 to about 11, from about 8 to about 10, about 8, about 9, about 10 or about 11.

The liquid embolic polymers, solutions, and mixtures described herein can be sterilized without substantially degrading the polymer. After sterilization, at least about 50%, about 60%, about 70%, about 80%, about 90%, about 95% about 99% or about 100% of the polymer can remain intact. In one embodiment, sterilization can be by autoclaving and can be utilized before administration of the polymer.

The liquid embolic polymer formulation can be removed from a vial using a needle and syringe, and the syringe can be later connected to a delivery device or catheter. Alternatively, the liquid embolic polymer formulation can be prepackaged in a delivery syringe.

To prevent premature liquid embolic polymer deposition, a delivery device or catheter can be primed with a bolus of the same flushing solution or similar water-miscible organic solvent and/or non-physiological pH aqueous solution as used to dissolve the liquid embolic polymer. This flushing can prevent clogging of the delivery catheter with the liquid embolic polymer. The syringe containing the liquid embolic formulation can then be connected to the proximal end of a delivery catheter, such as a microcatheter, cannula, or the like, and positioned in the desired anatomical site.

As the liquid embolic formulation is injected, it can push the solvent flushing solution out of the microcatheter. The solubility of the liquid embolic polymer can then rapidly change as it is exposed to physiological conditions. The progress of the liquid embolic formulation inside the delivery catheter can be observed using an imaging technique compatible with the covalently linked visualization agent or agents selected. With continued injection, the liquid embolic formulation can enter a target delivery site as a solid mass.

The aqueous nature of physiological conditions can reduce the solubility of the liquid embolic polymer and cause it to precipitate from the water-miscible, organic solvent. Alternatively or in addition to the aqueous nature of the physiological conditions, the large buffering capacity of the body's tissues can cause pH of the fluids to change rapidly thus reducing the solubility of the liquid embolic polymer and causing it to precipitate from solution. The precipitated liquid embolic polymer can provide occlusion of a target site.

Over time, the biodegradable linkages binding the visualization agents to the liquid embolic polymer can be broken and the visualization of the liquid embolic polymer can be diminished. In some embodiments, about 40%, about 50%, about 60%, about 70% about 80%, about 90%, about 95%, about 99% or about 100% of the biodegradably linked visualization agents can remain intact after about 5 days, about 2 weeks, about 1 month, about 2 months, about 6 months, about 9 months, about a year, about 2 years, about 5 years, about 10 years or about 20 years. Polymers can be fine tuned to degrade faster or slower.

The precipitated, solidified liquid embolic polymer can provide long-term occlusion of the target site. The precipitated liquid embolic polymer can remain substantially stable once implanted. For example, the liquid embolic polymer can remain greater than 60%, 70% 80%, 90%, 95%, or 99%, or nearly 100% intact after at least about 5 days, about 2 weeks, about 1 month, about 2 months, about 6 months, about 9 months, about a year, about 2 years, about 5 years, about 10 years or about 20 years.

In some embodiments, it may be desirable for the entire precipitated liquid embolic polymer to degrade over time. In such embodiments, the liquid embolic polymer can degrade to less than 40%, 30% 20%, 10%, 5% or 1% intact after at least about 5 days, about 2 weeks, about 1 month, about 2 months, about 6 months, about 9 months, about a year, about 2 years or about 5 years.

Further, the liquid embolic polymers once precipitated can be cohesive enough to stick to the tissue and/or remain in place through friction with the tissues and forces of circulating blood. In other embodiments, the precipitated polymer can act as a plug in a vessel held in place by the flow and pressure of the blood.

In one embodiment described herein, the liquid embolic polymer comprises a reaction product of 2-oxo-2-(1-oxo-1-(1-oxo-1-(2,4,6-triiodophenoxy)propan-2-yloxy)propan-2-yloxy)ethoxy)ethyl acrylate, hydroxyethyl methacrylate, and azobisisobutyronitrile. In another embodiment, the liquid embolic polymer comprises a reaction product of between about 75% and about 98% 2-oxo-2-(1-oxo-1-(1-oxo-1-(2,4,6-triiodophenoxy)propan-2-yloxy)propan-2-yloxy)ethoxy)ethyl acrylate, between about 2% and about 25% hydroxyethyl methacrylate, and less than about 1% azobisisobutyronitrile. In still another embodiment, the liquid embolic polymer comprises a reaction product of between about 85% and about 98% 2-oxo-2-(1-oxo-1-(1-oxo-1-(2,4,6-triiodophenoxy)propan-2-yloxy)propan-2-yloxy)ethoxy)ethyl acrylate, between about 2% and about 15% hydroxyethyl methacrylate, and less than about 1% azobisisobutyronitrile.

In another embodiment described herein, the liquid embolic polymer comprises a reaction product of 1-((2-(methacryloyloxy)ethoxy)carbonyloxy) ethyl 3,5-diacetamido-2,4,6-triiodobenzoate, hydroxyethyl methacrylate, and azobisisobutyronitrile. In another embodiment, the liquid embolic polymer comprises a reaction product of between about 85% and about 98% 1-((2-(methacryloyloxy)ethoxy)carbonyloxy) ethyl 3,5-diacetamido-2,4,6-triiodobenzoate, between about 2% and about 15% hydroxyethyl methacrylate, and less than about 1% azobisisobutyronitrile.

In still another embodiment described herein, the liquid embolic polymer comprises a reaction product of 1-((2-(methacryloyloxy)ethoxy)carbonyloxy) ethyl 3,5-diacetamido-2,4,6-triiodobenzoate, N-(3-Aminopropyl)methacrylamide hydrochloride, and azobisisobutyronitrile. In another embodiment, the liquid embolic polymer comprises a reaction product of about 74% 1-((2-(methacryloyloxy)ethoxy)carbonyloxy) ethyl 3,5-diacetamido-2,4,6-triiodobenzoate, about 26% N-(3-Aminopropyl)methacrylamide hydrochloride, and less than about 1% azobisisobutyronitrile.

EXAMPLE 1

Preparation of an Iodine-containing Monomer

A. To 250 mL of toluene, 15 g 2,4,6-triiodophenol, 22.9 g 3,6-dimethyl-1,4dioxane-2,5 dione, and 25 µL of stannous octoate were added. The solution was refluxed for 18 hr. After cooling the solution to 25° C., 3 mL acryloyl chloride and 5.2 mL triethylamine dissolved in 50 mL toluene were added. The mixture was stirred for 5 hr, filtered, washed with water, and dried under vacuum.

B. To 2400 mL of toluene, 120.0 g 2,4,6-triiodophenol, 73.2 g 3,6-dimethyl-1,4-dioxane-2,5-dione, 29.4 g glycolide, and 200 µL stannous octoate were added. The solution was refluxed for 24 hours. After cooling the solution to 25° C., 24.8 mL acryloyl chloride and 42.4 mL triethylamine were added. The mixture was stirred for 18 hours, filtered, and dried under vacuum.

EXAMPLE 2

Preparation of an Gadolinium-Containing Monomer

To 50 mL of dimethylformamide, 17.5 g gadolinium diethylene triamine pentaacetic acid, 13 g 3,6-dimethyl-1, 4-dioxane-2,5 dione, and 25 µL of stannous octoate were added. The solution was refluxed for 18 hr. After cooling the solution to 10° C., 3 mL acryloyl chloride and 5.2 mL triethylamine dissolved in 50 mL dimethylformamide were added. The mixture was stirred for 18 hr, filtered, and the solvent was removed.

EXAMPLE 3

Preparation of Another Iodine-Containing Monomer

To 400 mL of methanol was added 104 g (170 mmol) of diatrizoic acid followed by 28 g of cesium carbonate (65 mmol). After stirring for 45 min the methanol was removed in vacuo and the solids suspended in 500 mL diethyl ether. The solids were then collected on a Buchner funnel, dried in vacuo, to yield 120 g, (95%) of cesium diatriozate.

To 24 mL of HEMA (200 mmol) in 1000 mL of dry ether was added 16.8 mL (213 mmol) of pyridine at 4-10° C., under argon. To this solution was added 21.3 mL (200 mmol) of 1-chloroethyl chlorocarbonate, drop wise with stirring over 0.5 hour. After stirring for 0.5 hour at 4-10° C., the heavy precipitate was removed by filtration and the filtrate was concentrated to an oil in vacuo, yielding 44 g (100%) of HEMA-1-chloroethyl carbonate.

To 44 g (200 mmol) of HEMA-1-chloroethyl carbonate in 400 mL of anhydrous DMF, was added 30 g (40 mmol) of cesium diatriozate at 100° C., under argon, with good stirring. After 15 minutes another 40 g (54 mmol) of cesium diatriozate was added at 100° C., under Ar, with good stirring followed by a final 30 g (40 mmol), under the same conditions, for a total of 110 g cesium diatriozate (134 mmol). The reddish brown reaction mixture was heated at 100° C. for an additional hour and the solvent was removed in vacuo. The reddish brown solid residue was suspended in 1000 mL of dry ether and the solids collected on a Buchner funnel. After the solids were dried in vacuo they were suspended in 500 mL distilled water at 2000 rpm and the pH of the mixture adjusted to 8-9 with cesium carbonate. After stirring for 10 min the suspension was filtered and the solids washed 3×100 mL of distilled water, dried overnight in vacuo and crushed to a fine powder. Solid residue was again suspended in 1000 mL of dry ether and the solids collected on a Buchner funnel. After the solids were dried in vacuo again and crushed to a fine powder again they were purified by silica gel chromatography using a 1.5 Kg column and a 0-10% gradient of MeOH in dichloromethane, over 1 hour. This yielded 26 g (18%), very pale yellow crystalline solid.

EXAMPLE 4

Preparation of an Iodine-Containing Polymer

A. To 3 mL of dimethyl sulfoxide, 1.8 g triiodophenol chain extended with an average of 5 lactide units and capped with an acrylate, 0.2 g of hydroxyethyl methacrylate, and 10 mg of azobisisobutyronitrile were added. Upon complete dissolution of all components, the solution was placed at 80° C. for 4 hr. After cooling to room temperature, the polymer was recovered by precipitation in ethyl ether and dried under vacuum.

B. To a 10 mL vial was added 3 mL of dimethyl sulfoxide, 1.7 g of iodine monomer prepared in Example 1B, 0.3 g of hydroxyethyl methacrylate, and 10 mg of azobisisobutyronitrile. Upon complete dissolution of all components, the vial was degassed and sparged with argon. The solution was then placed in an 80° C. oven for 48 hours to polymerize. After cooling to room temperature, the polymer was recovered by precipitation in ethyl ether and dried under vacuum. It was then dissolved in THF, flashed on a silica column, then redissolved in THF. It was then precipitated in water and then lyophilized to yield the dry polymer product.

EXAMPLE 5

Preparation of an Iodine-Containing Polymer

To 14 g of dimethylformamide, 8 g of the iodine containing monomer prepared in Example 3, 1.4 g of hydroxyethyl methacrylate and 47 mg of azobisisobutyronitrile were added. Upon complete dissolution of all components the solution was placed at 80° C. for 48 hr. After cooling to room temperature, the polymer was recovered by precipitation in ethyl ether and dried under vacuum.

EXAMPLE 6

Preparation of an Iodine-Containing Polymer

To 6 g of n-methyl-2-pyrrolidone, 1.7 g of the iodine containing monomer prepared in Example 3, 0.25 g of aminopropylmethacrylamide and 10 mg of azobisisobutyronitrile were added. Upon complete dissolution of all components the solution was placed at 80° C. for 8 hr. After cooling to room temperature, the polymer was recovered by precipitation in ethyl ether and dried under vacuum.

EXAMPLE 7

Precipitation

Iodine containing polymers were dissolved in their respective solvents, e.g. aqueous soluble polymers were dissolved in pH 3 buffered solution and organic soluble iodine containing polymers were dissolved in dimethyl sulfoxide. The solutions were dispensed into 0.1 M phosphate buffered saline solution. The precipitate formed was ranked from 1 to 5, with 1 being least cohesive and 5 being most cohesive.

| Sample | Iodine monomer | Solvent | Cohesiveness |
|--------|----------------|---------|--------------|
| 1 | Triiodophenol | DMSO | 4 |
| 2 | Diatrizoic acid | DMSO | 4 |
| 3 | Diatrizoic acid | pH 3 buffer | 3 |

The examples above show that variations in cohesiveness can be achieved by variations in the formulation.

EXAMPLE 8

Flow

In a flow model, liquid embolic formulations were delivered through 0.017" I.D. microcatheters. The formulations were assessed visually for cohesiveness, injection pressure, plug formation and precipitation speed. Precipitation speed was ranked slow, medium and fast. All others were ranked 1 to 5 with 1 being least desired and 5 being most desired.

| Sample | Iodine Monomer | Precipitation Speed | Cohesiveness | Injection Pressure | Plug Formation |
|---|---|---|---|---|---|
| 1 | Triiodophenol | Fast | 3 | 5 | 4 |
| 4 | Diatrizoic acid | Slow | 4 | 4 | 5 |
| 5 | Diatrizoic acid | Medium | 4 | 5 | 4 |

The examples above show that variations in flow properties can be achieved by variations in the formulation.

EXAMPLE 9

Preparation of Liquid Embolic Formulation

To 9 g of dimethyl sulfoxide, 1 g of the polymer of Example 3 was added. The liquid embolic formulation was then aliquoted into vials and capped. The vials were autoclaved at 121° C. for 15 min.

EXAMPLE 10

Titration of the Iodine Content of the Polymer

Using the techniques described in Examples 1 and 3, the polymers described in the table were prepared. The iodine content of the polymers was investigated using an inductively coupled plasma-mass spectroscopy technique.

| Polymer | Fraction t-butyl acrylate | Fraction Example 1 monomer | Iodine Concentration (ug/g) |
|---|---|---|---|
| 1 | 0.55 | 0.45 | 186,000 |
| 2 | 0.4 | 0.6 | 289,000 |
| 3 | 0.25 | 0.75 | 309,000 |
| 4 | 0.1 | 0.9 | 329,500 |

The results of the above table show how the iodine content of the liquid embolic polymer can be controlled by the amount of iodine containing monomer used in the preparation of the polymer.

EXAMPLE 11

In Vivo Evaluation of the Liquid Embolic Device—Rabbit Kidney

Figure 2:
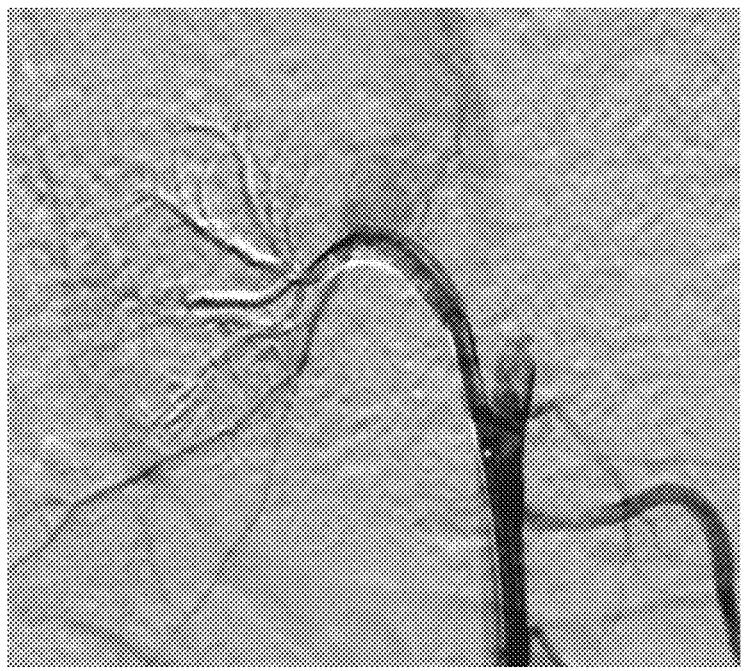
FIG. 2 illustrates a post-treatment angiogram of a rabbit kidney after use of an embodiment of an embolic polymer.

The liquid embolic formulation prepared according to the techniques of Examples 4, 5, and 6 was utilized for the embolization of a rabbit kidney. Angiographic occlusion was obtained in the kidney both before the procedure (FIG. 1) and after the procedure (FIG. 2). As illustrated, blood flow to the kidney is substantially depleted and replaced with an embolic polymer in FIG. 2. The vessels in FIG. 2 are visible in angiogram.

EXAMPLE 12

CT Evaluation of the Liquid Embolic Device

Figure 3:
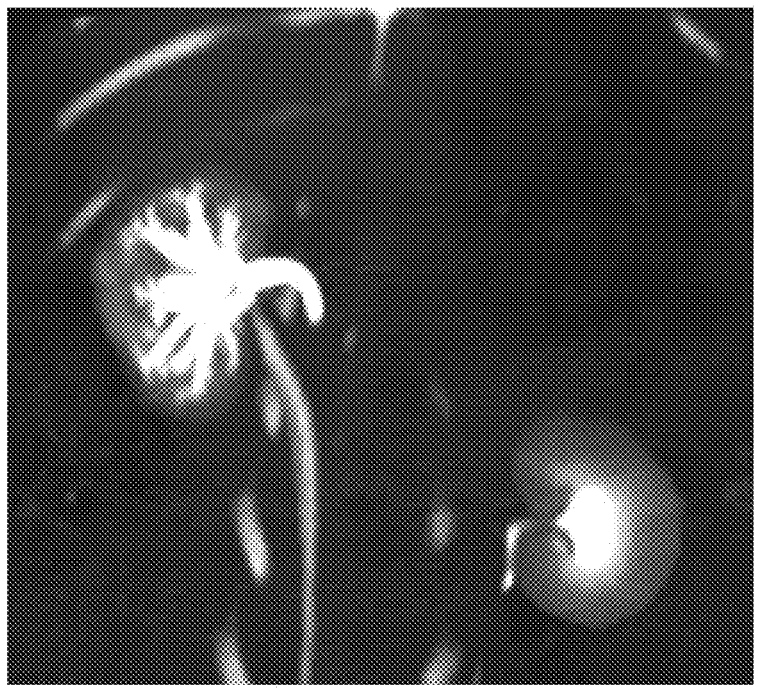
FIG. 3 illustrates a post-treatment CT scan of a rabbit kidney after use of an embodiment of an embolic polymer.

The liquid embolic formulation prepared according to the techniques of Examples 1, 2, and 3 was utilized for the embolization of the renal vasculature of rabbits. At the end of the procedure, the rabbit were imaged using a CT scanner. When comparing blood flow to the kidney in FIG. 1 to the vasculature filled with CT visible embolic polymer in FIG. 3, it is clear that blood flow in FIG. 1 has been replaced by embolic polymer in FIG. 3.

EXAMPLE 13

MR Evaluation of the Liquid Embolic Device

Figure 4:
FIG. 4 illustrates a post-treatment angiogram of a rabbit kidney after use of an embodiment of an embolic polymer.
Figure 5:
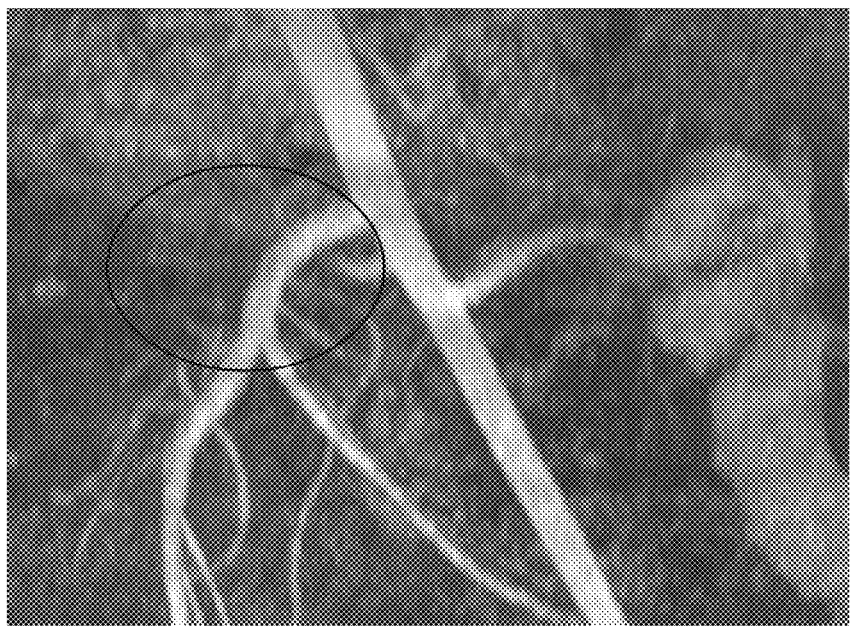
FIG. 5 illustrates a post-treatment MR scan of a rabbit kidney after use of an embodiment of an embolic polymer.

The liquid embolic formulation prepared according to the techniques of Examples 1, 2, and 3 was utilized for the embolization of the renal vasculature of rabbits. At the end of the procedure, the rabbit were imaged using a MR scanner. FIG. 4 illustrates an angiogram of the kidney including visible replacement of blood flow with liquid embolic polymer visible under an angiogram. FIG. 5 illustrates the embolic polymer visibility under MR angiography.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymer including:
   a biodegradable linkage to a visualization agent wherein the visualization agent is formed from a monomer having at least one aromatic ring and at least one polymerizable moiety,
   wherein the polymer is substantially stable and wherein the polymer is soluble in a non-physiological solution and insoluble in a physiological solution,
   wherein substantially stable is where the polymer is greater than 90% intact after about 1 month after an implantation procedure.

2. The polymer of claim 1, wherein the biodegradable linkage is Seq. ID 1, Seq. ID 2, Seq. ID 3, Seq. ID 4, Seq. ID 5, Seq. ID 6, Seq. ID 7, Seq. ID 8, Seq. ID 9, Seq. ID 10, Seq. ID 11, Seq. ID 12, or Seq. ID 13.

3. The polymer of claim 1, wherein the biodegradable linkage is an ester or a polyester.

4. The polymer of claim 1, wherein a monomer included in the polymer is 2-oxo-2-(1-oxo-1-(1-oxo-1-(2,4,6-triiodophenoxy)propan-2-yloxy)propan-2-yloxy)ethoxy)ethyl acrylate.

5. The polymer of claim 1 including a monomer including at least one hydroxyl group.

6. The polymer of claim 5, wherein the monomer is an acrylate.

7. The polymer of claim 6, wherein the acrylate is hydroxyethyl methacrylate.

8. The polymer of claim 1, wherein the non-physiological solution is dimethyl formamide.

9. The polymer of claim 1, wherein the non-physiological solution is dimethyl sulfoxide.

10. The polymer of claim 1 including a reaction product of between about 75% and about 98% 2-oxo-2-(1-oxo-1-(1-oxo-1-(2,4,6-triiodophenoxy)propan-2-yloxy)propan-2-yloxy)ethoxy)ethyl acrylate, between about 2% and about 25% hydroxyethyl methacrylate, and less than 1% azobisisobutyronitrile.

11. The polymer of claim 1 including a reaction product of between about 85% and about 98% 1-((2-(methacryloyloxy)ethoxy)carbonyloxy) ethyl 3,5-diacetamido-2,4,6-triiodobenzoate, between about 2% and about 15% hydroxyethyl methacrylate, and less than 1% azobisisobutyronitrile.

12. The polymer of claim 1, wherein substantially stable is where the polymer is greater than 60% intact after about 1 year after the implantation procedure.

13. The polymer of claim 1, wherein substantially stable is where the polymer is greater than 60% intact after about 5 years after the implantation procedure.

14. The polymer of claim 1, wherein substantially stable is where the polymer is greater than 90% intact after about 2 months after the implantation procedure.

15. The polymer of claim 1, wherein substantially stable is where the polymer is greater than 80% intact after about 6 months after the implantation procedure.

* * * * *

```
                            SEQUENCE LISTING

<160> NUMBER OF SEQ ID NOS: 13

<210> SEQ ID NO 1
    <211> LENGTH: 8
    <212> TYPE: PRT
    <213> ORGANISM: Artificial Sequence
    <220> FEATURE:
    <223> OTHER INFORMATION: Synthetic cleavable linkage

<400> SEQUENCE: 1

Gly Pro Gln Gly Ile Ala Ser Gln
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: Synthetic cleavable linkage

<400> SEQUENCE: 2

Gly Pro Gln Pro Ala Gly Gln
    1               5

<210> SEQ ID NO 3
    <211> LENGTH: 7
    <212> TYPE: PRT
    <213> ORGANISM: Artificial Sequence
    <220> FEATURE:
    <223> OTHER INFORMATION: Synthetic cleavable linkage

<400> SEQUENCE: 3

Gly Pro Gln Gly Ala Gly Gln
    1               5

<210> SEQ ID NO 4
    <211> LENGTH: 9
    <212> TYPE: PRT
    <213> ORGANISM: Artificial Sequence
    <220> FEATURE:
    <223> OTHER INFORMATION: Synthetic cleavable linkage

<400> SEQUENCE: 4

Lys Pro Leu Gly Leu Lys Ala Arg Lys
    1               5

<210> SEQ ID NO 5
    <211> LENGTH: 7
    <212> TYPE: PRT
```

```
<213> ORGANISM: Artificial Sequence
<220> FEATURE:
<223> OTHER INFORMATION: Synthetic cleavable linkage

<400> SEQUENCE: 5

Gly Pro Gln Ile Trp Gly Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic cleavable linkage

<400> SEQUENCE: 6

Gln Pro Gln Gly Leu Ala Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic cleavable linkage

<400> SEQUENCE: 7

Gly Phe Gln Gly Val Gln Phe Ala Gly Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic cleavable linkage

<400> SEQUENCE: 8

Gly Phe Gly Ser Val Gln Phe Ala Gly Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic cleavable linkage

<400> SEQUENCE: 9

Gly Phe Gly Ser Tyr Phe Phe Ala Gly Phe
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic cleavable linkage

<400> SEQUENCE: 10

Gly Gly Leu Gly Pro Ala Gly Gly Lys
1               5

<210> SEQ ID NO 11
<211> LENGTH: 4
<212> TYPE: PRT
<213> ORGANISM: Artificial Sequence
```

```
<220> FEATURE:
<223> OTHER INFORMATION: Synthetic cleavable linkage

<400> SEQUENCE: 11

Ala Pro Gly Leu
1

<210> SEQ ID NO 12
<211> LENGTH: 4
<212> TYPE: PRT
<213> ORGANISM: Artificial Sequence
<220> FEATURE:
<223> OTHER INFORMATION: Synthetic cleavable linkage

<400> SEQUENCE: 12

Gly Phe Leu Gly
1

<210> SEQ ID NO 13
<211> LENGTH: 5
<212> TYPE: PRT
<213> ORGANISM: Artificial Sequence
<220> FEATURE:
<223> OTHER INFORMATION: Synthetic cleavable linkage

<400> SEQUENCE: 13

Asp Glu Val Asp Thr
1               5
```